(12) United States Patent
Slizynski et al.

(10) Patent No.: US 9,445,742 B2
(45) Date of Patent: *Sep. 20, 2016

(54) ELECTRICAL IMPEDANCE TECHNIQUES IN TISSUE-MASS DETECTION AND CHARACTERIZATION

(71) Applicants: Roman A. Slizynski, Corona, CA (US); David J. Mishelevich, Paya del Rey, CA (US)

(72) Inventors: Roman A. Slizynski, Corona, CA (US); David J. Mishelevich, Paya del Rey, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/719,328

(22) Filed: May 22, 2015

(65) Prior Publication Data

US 2015/0272470 A1  Oct. 1, 2015

Related U.S. Application Data

(63) Continuation-in-part of application No. 13/300,600, filed on Nov. 20, 2011, now Pat. No. 9,042,976, which is a continuation-in-part of application No. 12/874,192, filed on Sep. 1, 2010, now Pat. No. 9,037,227.

(60) Provisional application No. 61/238,949, filed on Sep. 1, 2009.

(51) Int. Cl.
   *A61B 5/053* (2006.01)
   *A61B 5/00* (2006.01)
   *A61B 6/00* (2006.01)
   *A61B 8/08* (2006.01)

(52) U.S. Cl.
   CPC ............ *A61B 5/0536* (2013.01); *A61B 5/0035* (2013.01); *A61B 5/053* (2013.01); *A61B 5/4312* (2013.01); *A61B 5/6867* (2013.01); *A61B 5/726* (2013.01); *A61B 5/7253* (2013.01); *A61B 5/7257* (2013.01); *A61B 6/5247* (2013.01); *A61B 8/5261* (2013.01)

(58) Field of Classification Search
   CPC .. A61B 5/4312; A61B 5/053; A61B 5/0536; A61B 5/0537; A61B 2017/00026
   USPC .................... 600/682, 407, 442, 547; 606/34
   See application file for complete search history.

(56) References Cited

U.S. PATENT DOCUMENTS

| | | | |
|---|---|---|---|
| 9,037,227 B2* | 5/2015 | Slizynski | A61B 5/053 600/547 |
| 9,042,976 B2* | 5/2015 | Slizynski | A61B 5/053 600/547 |
| 2004/0152997 A1* | 8/2004 | Davies | A61B 5/04002 600/547 |

* cited by examiner

*Primary Examiner* — Adam J Eiseman

(57) ABSTRACT

A device is described for measuring electrical characteristics of biological tissues with plurality of electrodes and a processor controlling the stimulation and measurement in order to detect the presence of abnormal tissue masses in organs. Examples of suitable organs are the breast, skin, oral cavity, lung, liver, colon, rectum, cervix, and prostate and determine probability of tumors containing malignant cancer cells being present in tissue. The approach can also be applied to biopsied tissue samples. The device has the capability of providing the location of the abnormality. The method for measuring electrical characteristics includes placing electrodes and applying a voltage waveform in conjunction with a current detector. A mathematical analysis method is then applied to the collected data, which computes spectrum of frequencies and correlates magnitudes and phases with given algebraic conditions to determine mass presence and type.

12 Claims, 16 Drawing Sheets

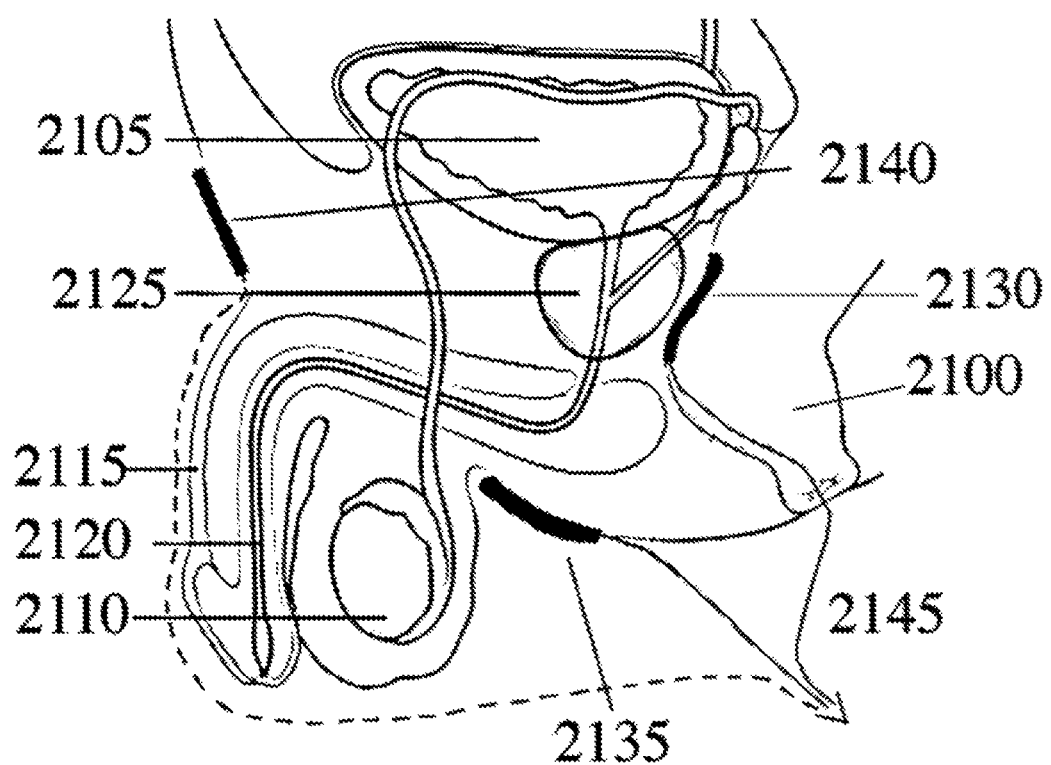

ELECTRICAL IMPEDANCE TECHNIQUES IN TISSUE-MASS DETECTION AND CHARACTERIZATION

CROSS REFERENCE TO RELATED APPLICATIONS

This patent application claims priority as a continuation-in-part of U.S. patent application Ser. No. 13/300,600 filed Nov. 20, 2011 entitled "USE OF IMPEDANCE TECHNIQUES IN BREAST-MASS DETECTION," that is a continuation-in-part of U.S. patent application Ser. No. 12/874,192 filed Sep. 1, 2010 entitled "USE OF IMPEDANCE TECHNIQUES IN BREAST-MASS DETECTION," and also claims priority to U.S. provisional application Ser. No. 61/238,949 filed on Sep. 1, 2009 entitled "USE OF IMPEDANCE TECHNIQUES IN BREAST-MASS DETECTION." The disclosures of each of these patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually cited to be incorporated by reference.

REFERENCES

[1] Ruigang Liu, Xiuzhen Dong, Feng Fu, Fusheng You, Xuetao Shi, Zhenyu Ji, Kan Wang, *Multi-frequency parameter mapping of electrical impedance scanning using two kinds of circuit model*. Physiological Measurement: July 2007 Volume: 28 Start Page: S85.

[2] Tyna A Hope and Sian E Iles, *The use of electrical impedance scanning in the detection of breast cancer.* Breast Cancer Res. 2004; 6(2): 69-74.

[3] J. Jossinet and B. Lavandier, *The discrimination of excised cancerous breast tissue samples using impedance spectroscopy*, Bioelectrochemistry and Bioenergetics, Volume 45, Issue 2, May 1998, Pages 161-167

[4] Arum Han, Lily Yang and A. Bruno Frazier, *Quantification of the Heterogeneity in Breast Cancer Cell Lines Using Whole-Cell Impedance Spectroscopy*, Clinical Cancer Research 13, 139, Jan. 1, 2007. doi: 10.1158/1078-0432.CCR-06-1346.

[5] Alexander Stojadinovic, Aviram Nissan, Zahava Gallimidi, Sarah Lenington, Wende Logan, Margarita Zuley, Arieh Yeshaya, Mordechai Shimonov, Moshe Melloul, Scott Fields, Tanir Allweis, Ron Ginor, David Gur, and Craig D. Shriver, *Electrical Impedance Scanning for the Early Detection of Breast Cancer in Young Women: Preliminary Results of a Multicenter Prospective Clinical Trial*, Journal of Clinical Oncology, Volume 23, Number 12, Apr. 20, 2005: 2703-2715.

[6] WANG Kan, WANG Ting, FU Feng, JI Zhen-yu, LIU Rui-gang, LIAO Qi-mei and DONG Xiu-zhen, *Electrical impedance scanning in breast tumor imaging: correlation with the growth pattern of lesion,* Chinese Medial Journal 2009; 122(13):1501-1506.

[7] T. Morimotoa, Y. Kinouchib, T. Iritanic, S. Kimura Y. Konishia, N. Mitsuyamaa, K. Komakia, Y. Mondena, *Measurement of the Electrical Bio-Impedance of Breast Tumors*, European Surgical Research Vol. 22, No 2, 1990; 22:86-92 (DOI: 10.1159/000129087).

[8] Alexander Stojadinovic, M.D., Aviram Nissan, M.D., Craig D. Shriver M.D., Sarah Lenington, Ph.D., David Gur, Sc.D, *Electrical Impedance Scanning for Breast Cancer Risk Stratification in Young Women*, Hermann Scharfetter, Robert Merva (Eds.): ICEBI 2007, IFMBE Proceedings 17, pp. 675-678, 2007.

[9] Mohr, P. Ulrik Birgersson, P. U., Berking, C., Henderson, C., Trefzer, U., Kemeny, L., Cord Sunderkotter, C., Dirschka, T., Motley, R., Frohm-Nilsson, M, Reinhold, U., Loquai, C., Braun, R., Nyberg, F., and J. Paoli, *Electrical impedance spectroscopy as a potential adjunct diagnostic tool for cutaneous melanoma*, Skin Research and Technology 2013; 19:75-83 (doi: 10.1111/srt.12008).

[10] Yung, R. C., Zeng, M. Y., Stoddard, G. J., Garff, M, and K. Callahan, *Transcutaneous Computed Bioconductance Measurement in Lung Cancer*, Journal of Thoracic Oncology, Vol 7, Number 4, pp. 681-689, April, 2012.

[11] Laufer, S., Ivorra, A., Reuter, V. E., Rubinsky, B., and S. B., Solomon, *Electrical impedance characterization of normal and cancerous human hepatic tissue,* Physiol Meas. 2010 July; 31(7):995-1009. doi: 10.1088/0967-3334/31/7/009. Epub 2010 Jun. 24.

[12] Gupta, D., Lammersfeld, Carolyn A., Burrows, Jessica L., Dahlk, Sadie L., Vashi, P. G., Grutsch, J. F. Hoffman, Sra, and C. G. Lis, *Bioelectrical impedance phase angle in clinical practice: implications in advanced colorectal cancer,* Am. J. Clin. Nutr, 80:1634-8, 2004.

[13] Tidy, J. A., Brown, B. H., Healey, T. J., Daayana, S., Martin, M, Prendiville, W. and H C. Kitchenerg, *Accuracy of detection of high-grade cervical intraepithelial neoplasia using electrical impedance spectroscopy with colposcopy*, DOI: 10.1111/1471-0528.12096.

[14] Wan, Y., Borsic, A., Heaney, J., Seigne, J., Schned, A., Baker, M., Wason, S., Hartov, A, and R. Halter, *Transrectal Electrical Impedance Tomography of the Prostate: Spatially Co-registered Pathological Findings for Prostate Cancer Detection*, Med Phys 40:063102. 2013.

FIELD OF THE INVENTION

The application of a signal to tissue and differentiating tissue characteristics such as the presence of benign or malignant growths from normal tissue based on impedance characteristics.

BACKGROUND OF THE INVENTION

Bio-impedance of breast tumors has been a source for numerous scientific research studies since discovery of electricity by Volta in 1800. It was the Cole brothers (in 1930) who mathematically and physically described dielectric properties. Cole-Cole equations are used in bio-impedance analysis. Since the late 1960's, bio-impedance analysis has benefited from the advent of microprocessors and digital signal processing.

The method can also be used to characterize biological tissue electrical properties in many different applications including blood analysis, body muscle and fat content as well as in estimating the length of the root canal in teeth see U.S. Pat. No. 6,425,875 "Method and device for detection of tooth root apex."

Electrical Impedance Scanning (EIS) has been described in literature [1] [2] and machines have been built to be used on patients. The EIS of the breast relies on body transmission of alternating electricity using an electrical patch attached to the arm and a hand-held cylinder. The electrical signal flows through the breast where it is then measured at skin level by a probe placed on the breast. Examples of such devices are the T Scan 2000 from Mirabel Medical Systems, which has been cleared by the FDA for adjunctive diagnosis in conjunction with mammography, and the follow-on T Scan 2000 ED. Mirabel devices are covered under multiple patents among which are Andrew L. Pearlman (U.S. Pat. No. 7,141,019), Ron Ginor (U.S. Pat. No. 7,302,292) and Ginor and Nachaliel (U.S. Patent Application Pub. No. 2007/0293783). Other devices are the one from Biofield Corp. (Cuzick et al, U.S. Pat. No. 6,351,666), and the device of Richard J. Davies (U.S. Pat. Nos. 6,922,586 and 7,630,759).

The benefits of having a non-mammographic mechanism to screen for patients whose age is less that age 50 are significant. Below age of 40, radiation from use of screening mammography will cause more cancer than it saves. Between 40 and 50 there is a break even where one saves approximately as many of cancers caused. Above 50 years of age mammography works well because a tumor contrasts well against normal breast tissue. After age 50, fat content increases; since fat is darker, there is a contrast of normal breast tissue to cancer tissue. Below age 40 the density of the breast tissue is so high that it is difficult to impossible to differentiate from a tumor. The same is not quite as true for women in the age group of 40 to 50 but the problem with mammographic differentiation between normal breast tissue and cancer remains.

Asymptomatic young women under the age of 40 are not routinely screened (in the United States) but instead depending on breast self-examination (BSE) and clinical-breast examination (CBE). Carcinoma of the breast is generally more aggressive in younger women. The availability of a diagnostic test that does not involve radiation would be of significant benefit.

Mammograms only demonstrate presence of calcium and not all DCIS masses have calcium deposits. MRI and PET only detect increases in vascularity that may or may not be present. One consideration in mammography is that the results are not necessarily stable; some 30% of "cancer" detected on mammography disappears.

Another factor is the detection of breast cancer, and other abnormalities, is the cost of doing procedures. It would of significant benefit, particularly in developing countries, to have a low cost procedure. Of course, lower cost and resulting wider availability is important in developed nations as well.

SUMMARY OF THE INVENTION

Breasts can be examined using an electrical impedance scanning method, which has been previously described in many publications [1] [2] [3]. In this novel invention, the method is improved to quickly scan through multiple frequencies by using a complex waveform containing even and odd harmonics across several decades of frequencies.

Uses are:
1. Detection of Ductal Carcinoma In Situ (DCIS) other malignant tumor masses, or benign breast masses
2. Follow up of changes in masses over time
3. Assess effectiveness of treatment to eradicate DCIS or other tumors.

The invention provides significant benefits, first by avoiding use of radiation which can generate the cancers that mammography that the test is meant to detect and perhaps other cancers and second by offering a low-cost diagnostic test and tracking vehicle.

Impedance systems and methods can be applied to tissues from any part of the body to search for the detection of, location of, and characterization tissue abnormalities including differentiation between benign and malignant masses. Mohr et al. [9] addressed melanoma (using 35 different frequencies, logarithmically distributed from 1.0 kHz to 2.5 MHz), Yung et al. addressed the lung [10], Lauder et al. [11] the liver (in the frequency range of 1 to 400 kHz), Gupta et al. [12] the colon, Tidy et al. [13] the cervix (frequency ranging from 76.3 to 625 kHz in 14 steps), and Wan et al. [14] (frequencies of 0.4 kHz, 3.2 kHz and 25.6 kHz). All of the preceding do not use stimulation with simultaneous multiple frequencies and use standard impedance techniques rather than the ratio-metric approach that is the novelty of the current invention. This invention can be used in humans or animals.

The invention provides significant benefits, first by avoiding use of radiation which can generate the cancers that mammography that the test is meant to detect and characterize other cancers and second by offering a low-cost diagnostic test and tracking vehicle.

DETAILED DESCRIPTION OF THE INVENTION

The amplitude and phase of several harmonics within a range of frequencies creates a signature of the breast growths allowing differentiation of benign and malignant masses. Our invention is novel in that it differentiates normal from abnormal tissue based on observing secondary effects of changes in dielectric properties due to increased numbers of cells based on phase and amplitude of multiple levels of harmonics without the necessity to measure absolute capacitance and resistance values. The invention allows differentiation of benign masses (e.g., tumor or infections) versus malignant masses versus other cellular changes. Our approach is not impacted by patient-to-patient differences.

Other impedance-related approaches (e.g., those referenced above from Mirabel Medical Systems, Biofield, and Davies) depend on measuring absolute capacitive and absolute resistive properties to compute the Cole-Cole function shape. Measuring absolute values is difficult and inherently error prone, especially since they will vary from patient to patient.

To analyze measurements by searching for simultaneous interactions between multiple frequencies, the obvious choice is to use Fast Fourier Transform or Discrete Fourier Transform. However there other transforms that may give very specific and different advantages.

Chirp-Z Transform has an advantage of having the ability to focus analysis on specific band of frequencies by performing spectra zooming. The range of data points does not have to be equal to $2^n$ and in its zoomed form it can be continuously moved to mark time information of the analyzed data.

Chirp-Z Transform:

$$CZT(x[n]) = \sum_{n=0}^{N-1} x[n] \cdot z_k^{-n}$$

Wavelet Transform or Discrete Wavelet Transform has an ability to resolve time and frequencies within the uncertainty principle.

Wavelet Transform is two-dimensional:

$$CWT_x^\Psi(\tau, s) = \frac{1}{\sqrt{|s|}} \int x(t) \cdot \Psi * \left(\frac{t-\tau}{s}\right) dt$$

Uncertainty principle:

$$\Delta t \Delta f \geq \frac{1}{4\pi}$$

FFT/DFT transforms show interactions between frequencies and the same interactions will be shown when using Chirp-Z or Wavelet transform.

The additional information these last two transforms bring, while testing tissue, could be used to further mark the signature of these cells for differentiation.

Figure 1:
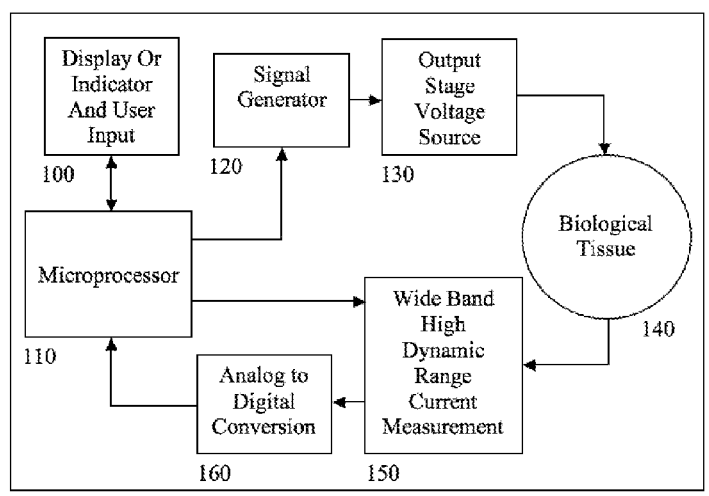
FIG. 1 shows a block diagram of the impedance application system.
Figure 11:
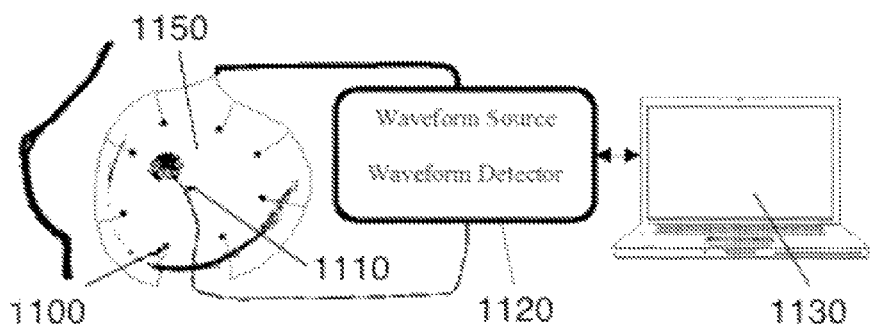
FIG. 11 illustrates the breast-impedance configuration with a multiple-electrode source.

An embodiment of a suitable device is shown in the Block Diagram of FIG. 1, which illustrates the block diagram of the invention for breast-mass detection. After the unit powers up through the use of user interface 100, the microprocessor 110 will load the characteristics of the desired square wave to the generator 120. If another wave type were used (e.g., sine or saw tooth), generator 120 would generate that wave type. As commanded by the medical professional through the input interface 100, the microprocessor 110 will start coherent sampling by synchronizing the waveform generation 120 and waveform capture 150. Output stage 130 assures proper voltage levels and their rising and falling edges. The output stage 130 also distributes the signal to multiple electrodes as shown in FIG. 11. Microprocessor 110 controls the main frequency and triggers the current capture 150. The biological tissue 140 is the breast under examination. The sampled current 150 is digitized by Analog to Digital Converter (ADC) 160. A Fast Fourier Transform (FFT) is computed by microprocessor 110 on $2^n$ samples received from ADC 160. For practical considerations, the n should be equal or greater than 8. Typically it would be 12, but with microprocessor advances this can be increased for better accuracy. The resulting FFT data with its magnitude and phase are compared by the microprocessor 110 with the identifying references stored in it. The references may include markers identifying benign or malignant tumors including their relative position to a probes being tested. All the conclusions of testing by the microprocessor 110 are sent to the display 100 to inform the medical professional. The circuit requires coherent source and sampling conditions to achieve the spectral resolution needed to precisely identify changes in amplitudes and phases caused by masses, including growing cancer cells. Coherent sampling is superior over any type of data windowing or interpolation. A wide spectral band is used from around 20 kHz to several MHz with odd harmonics. The non-linearities in the tissue will contribute to generation of even harmonics at much smaller amplitude. Our invention can be used in the ranges of 10 kHz to 1 MHz, or from 1 MHz to approximately 100 MHz, and from 100 MHz to 10 GHz.

Figure 2:
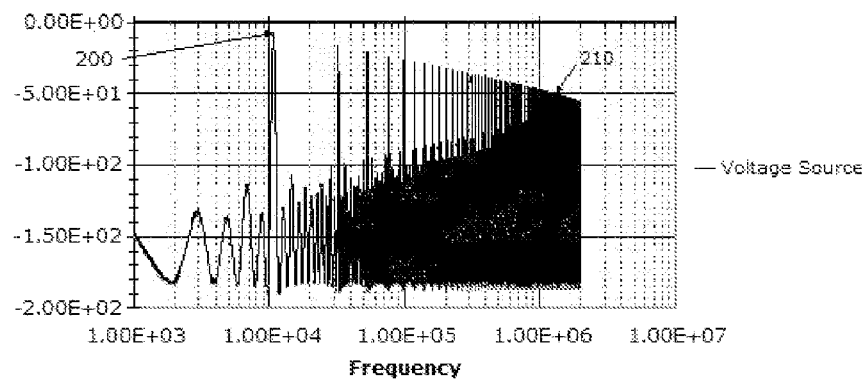
FIG. 2 illustrates the source waveform with all even and odd harmonics.

In one embodiment, the square wave main frequency 200 in FIG. 2 is set to 10.74219 kHz. This satisfies the coherency condition of 11 cycles, 4096 samples and 250 ns sampling. It places the $93^{rd}$ 210 harmonic at 999.0234 kHz. This setting takes into computation 48 harmonics. Research papers have indicated 100 kHz to 1 MHz to be affected by growing tumor cells [4] [5]. The square wave rising and falling edges were set to 250 ns giving odd harmonic content.

Figure 3:
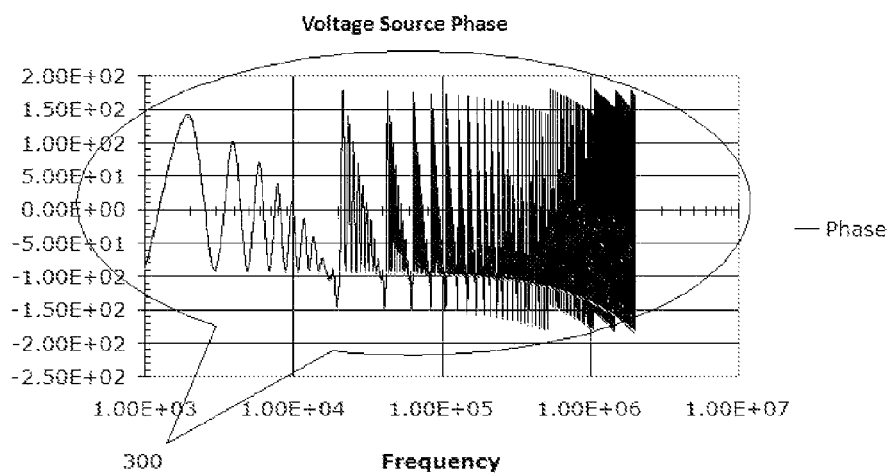
FIG. 3 shows the phase of the source waveform.

All harmonics in the band of the source square wave, as shown with their magnitude in FIG. 2 and the phase in FIG. 3, are used in the computation. The results of magnitude and phase changes 300 in FIG. 3 are compared with the set of the reference amplitudes and phases as they identify cancer cells [2] [6] [7] [8]. Alternatively, a set of reference amplitudes and phases as they identify masses of benign cells can be used.

Figure 4:
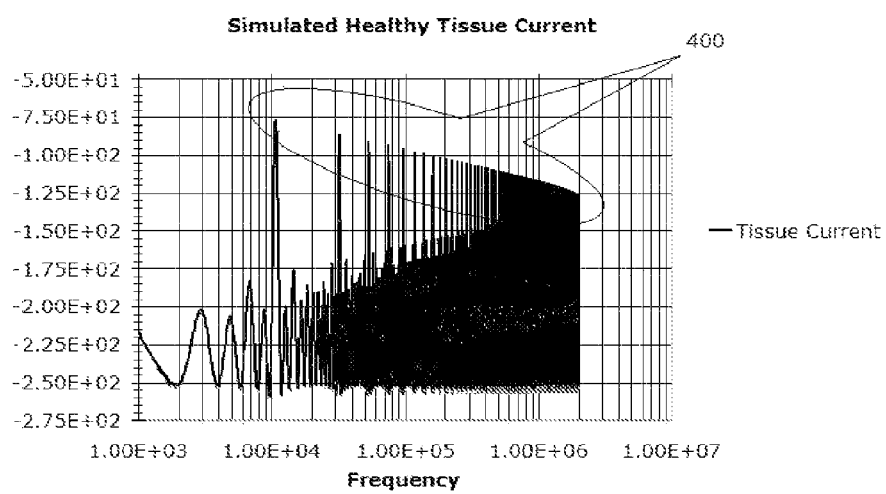
FIG. 4 illustrates the magnitude response of regular breast tissue.
Figure 5:
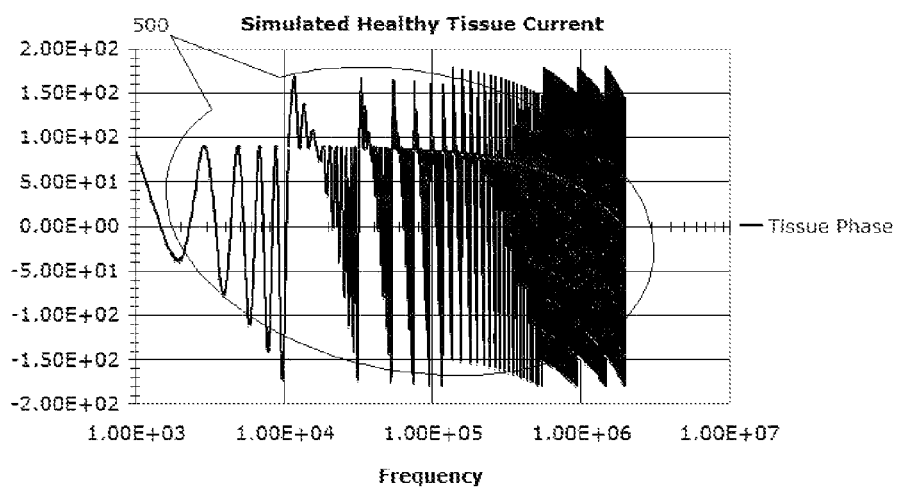
FIG. 5 shows the phase response of a regular breast tissue.
Figure 6:
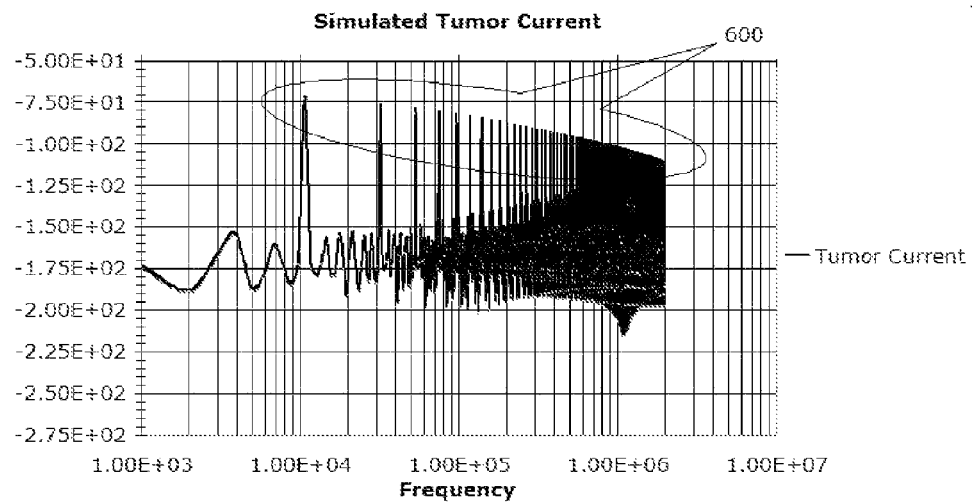
FIG. 6 illustrates the magnitude response of tumor tissue.
Figure 7:
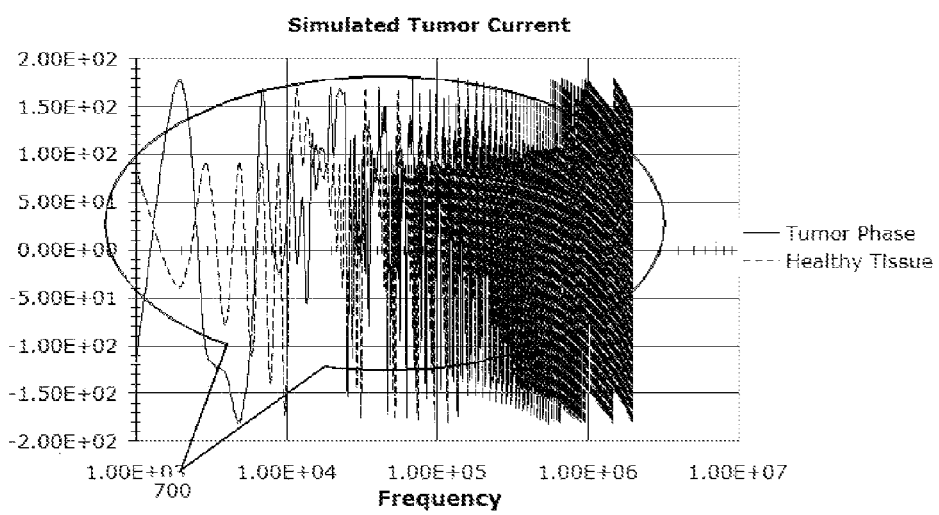
FIG. 7 shows the phase response of a regular and tumor tissue.

FIG. 4 shows an example of breast-tissue current with its magnitude response to the square-wave stimulus and FIG. 5 with its phase response. The model of a tumor tissue includes a non-linear capacitor. The harmonic level 400 in FIG. 4 is shifted to larger value. The phase plot 500 in FIG. 5 has changed shape. FIGS. 6 and 7 respectively show examples of breast-tissue current in magnitude 600 in FIG. 6 and phase responses to the square-wave stimulus for malignant breast tissue. FIG. 7 compares healthy tissue response with tumor tissue response 700.

The phase and amplitude changes across multiple frequencies differentiate the tissue into healthy cells, benign mass, and malignant tumor. The amount of phase shift at particular frequencies creates a marker to be identified during clinical studies. Having in excess of 40 harmonics, the cell signature makes the differentiation very visible.

Figure 8:
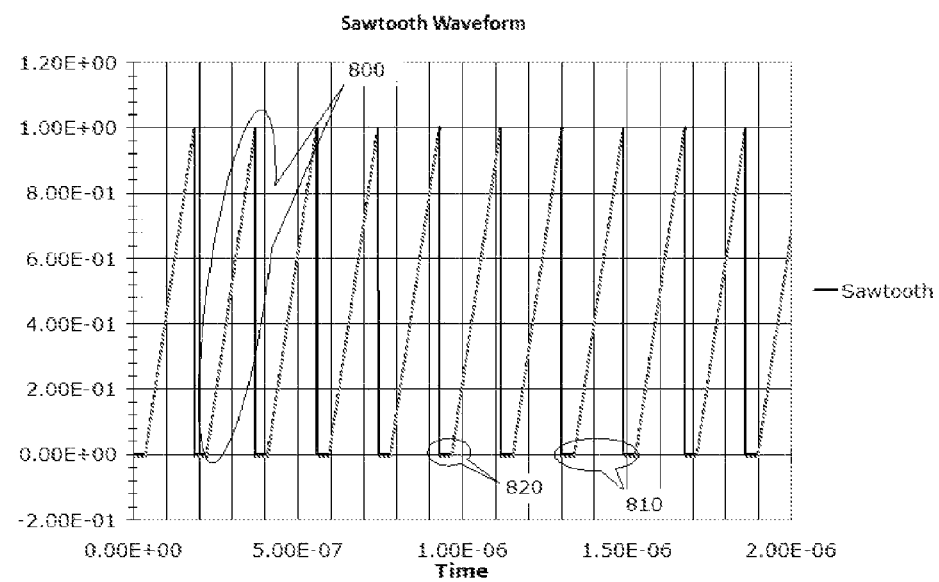
FIG. 8 shows saw tooth waveform.

Some of the scientific publications show analysis of dielectric properties of tumor cell in the frequency range up to 10 GHz. A modified saw tooth waveform 800 in FIG. 8 with coherent ratio between its period 810 and sampling interval would cover this range. The plateau 820 in the saw tooth could be made variable to tune in into the response of specific tumor cells.

Figure 9:
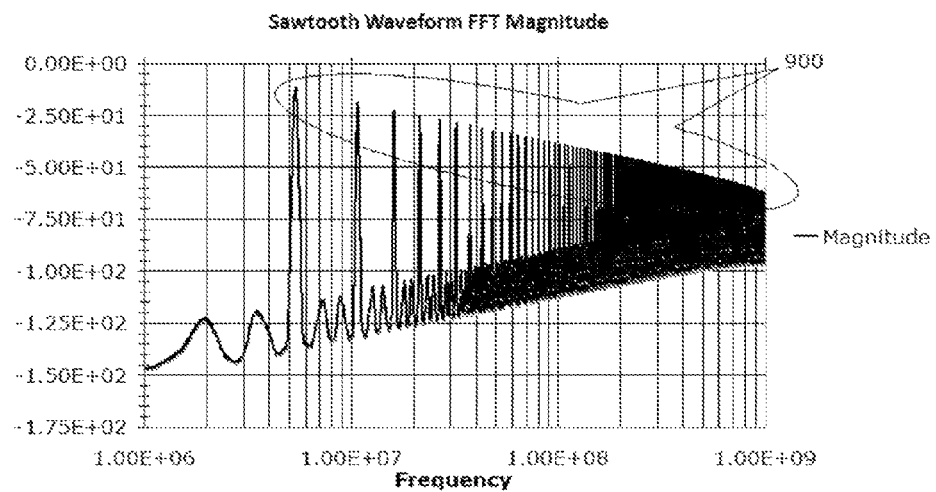
FIG. 9 shows the FFT magnitude of the saw tooth waveform.
Figure 10:
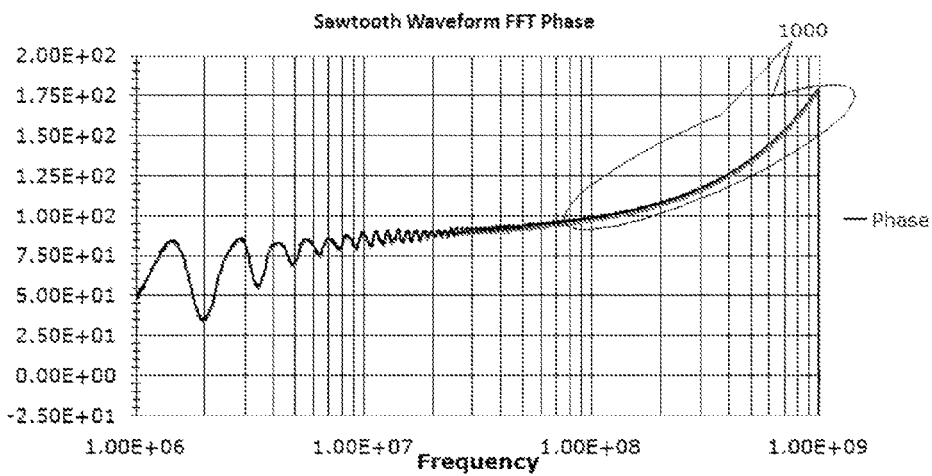
FIG. 10 shows the FFT phase of the saw tooth waveform.

The magnitude of Fast Fourier Transform is shown on FIG. 9. The waveform shows both even and odd harmonics 900. The phase response of the saw tooth waveform shown in FIG. 10 exhibits small variations in the bandwidth of interest 1000.

The waveform sources 1100 are distributed around the breast 1150 at constant separation angles as shown in FIG. 11. The nipple is used to connect the detector 1110. The connection can be made via a cap or other surface connection or via an inserted probe. Generating waveforms and collecting data are done by stand-alone device 1120. The resulting data are transferred to a computer 1130 for visual and mathematical analysis. The receiving electrode 1110 in FIG. 11 may be one covering the nipple, or for increased localization capability may be an electrode made of insulated wire with a bare conducting tip inserted into one of the (typically on the order of nine) milk ducts. The localization is in three dimensions. For differentiated signatures, this approaches permits greater localization. In another embodiment the source and receiving electrodes are incorporated in a brassiere. This electrode configuration can be effectively employed for screening where a mass is not palpable or the situation where a mass is palpable.

The ECG/EKG pads are distributed in the area where breast attaches to the chest wall. The ECG/EKG pads can be replaced with 30 gauge needles to achieve a higher degree of accuracy.

The system is not limited to the use of a square wave. A sine wave can be used with the same coherent setting for multiple frequencies covering similar or the same harmonics. There could be one sine wave source with a non-linear gain element creating harmonics without need to step the frequencies.

Analyzing magnitude and phase for over 40 harmonics in frequency span from 10 kHz to 1 MHz will be a substantial source for the signature differentiating dielectric properties of healthy tissues versus tumor tissue. Many publications show Cole-Cole charts with significant changes when tumor cell start to grow in this frequency span.

In other embodiments, the number of source electrodes is varied. The larger the number of source electrodes, the higher the resolution of localization. For example having eight source electrodes arranged around the perimeter of the breast will double the localization capability since the area of the breast will be divided into eight regions as opposed to quadrants. Where in some applications of the device, one only wants to do screening to know whether a lesion is likely present or not, in others being able to localize would be important. This may occur, for example, if one is tracking changes in the lesion. Tracking can be done by taking a base measurement, instilling a therapeutic agent in one or a plurality of milk ducts, and assessing the progress of treatment via follow-up measurements.

Figure 12:
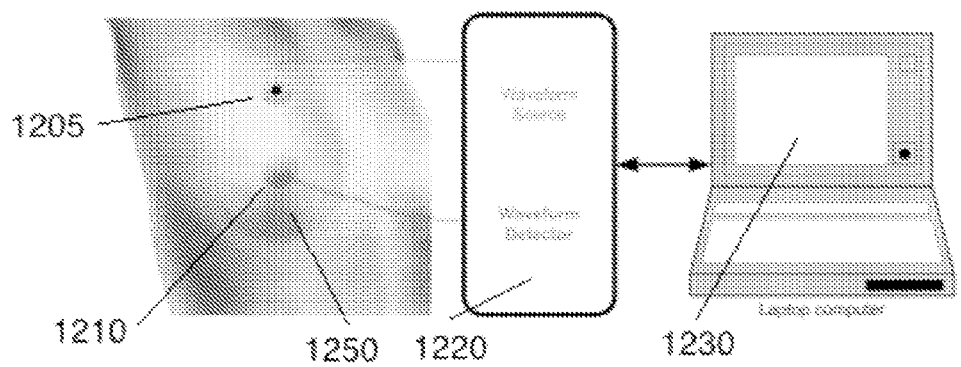
FIG. 12 illustrates the breast-impedance configuration with a single-electrode source.
Figure 13:
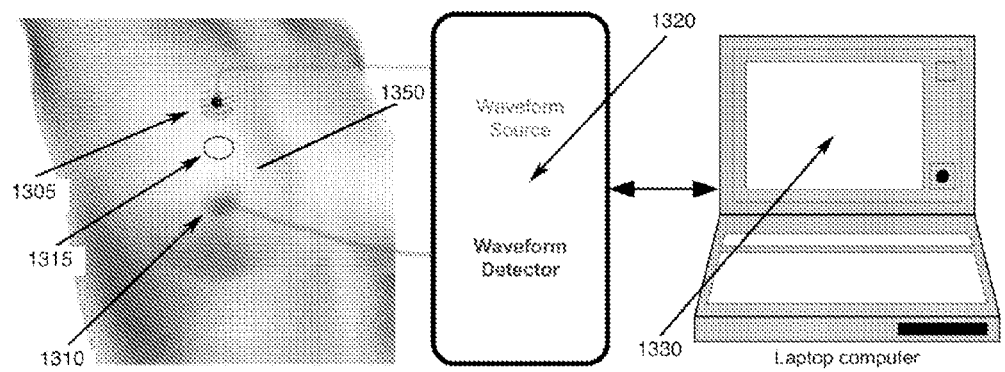
FIG. 13 illustrates the breast-impedance configuration with a single-electrode source and illustrating a breast mass.

An alternative source electrode configuration is shown in FIG. 12 for breast 1250. This has a single source probe electrode 1205 with receiving electrode 1210. Generating waveforms and collecting data is done by stand-alone device 1220. The resulting data is transferred to a computer 1230 for visual and mathematical analysis. The configuration of FIG. 13 shows the configuration of FIG. 12 in conjunction with breast 1350 containing an example lump 1315 characterized by employing source electrode (probe) 1305 and receiving electrode 1310. Generating waveforms and collecting data are done by stand-alone device 1320. The resulting data are transferred to a computer 1330 for visual and mathematical analysis. In this configuration, three-dimensional reconstruction is not required because the impedance characteristics would be determined for a single palpable mass over which the electrode is placed. In this mode, the device is used for evaluation of a given mass as opposed to screening for a non-palpable breast mass.

Figure 14:
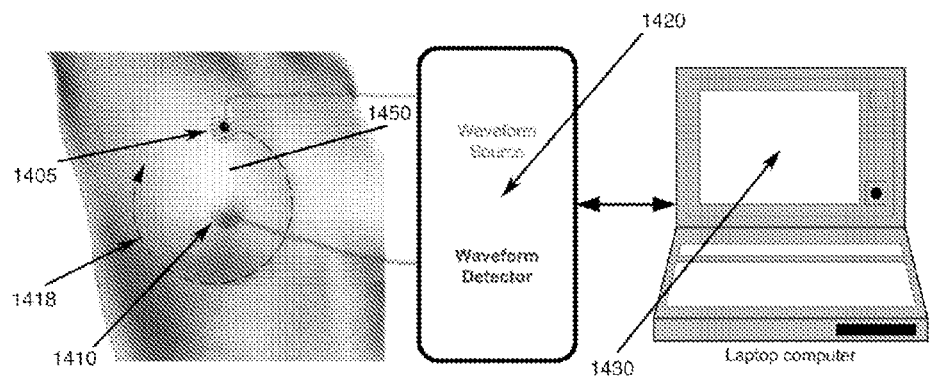
FIG. 14 illustrates the breast-impedance configuration with a single-electrode source showing the movement trajectory of that electrode to allow three-dimensional reconstruction.

FIG. 14 demonstrates a variation of configurations of FIGS. 12 and 13 in conjunction with breast 1450 in which source probe electrode 1405 is moved around the base of the breast 1450 with the single receiving electrode 1410. Generating waveforms and collecting data are done by stand-alone device 1420. The resulting data are transferred to a computer 1430 for visual and mathematical analysis. In this configuration, movement of the single-source probe electrode 1405 around the base of breast 1450 in a roughly circular trajectory allows data collection of the type in FIG. 11 in which a three-dimensional reconstruction and thus 3-D localization of a breast mass can be accomplished. The position of the single-source probe and its movement can be shown on the computer screen so the program knows for which location data is collected. Thus this configuration can be used for screening in which a breast mass can be detected and characterized through its signature, whether than mass was palpable or not.

Feedback to the user as to results may take multiple forms. In one embodiment, the presence an abnormality is a non-visual feedback. This is supplied by an auditory or vibratory cue. Tone patterns can provide either a binary or relative magnitude, including level of probability. In another embodiment, the presence of an abnormality is indicated by a simple visual cue such as an LED display, either binary or relative magnitude, including level of probability.

In another embodiment, the presence of an abnormality is indicated by an intermediate visual display presenting text or graphical results, including level of probability and 3-D location. In still another embodiment, the presence of an abnormality is indicate by a complex visual display presenting raw data and processed graphical information, including level of probability.

The invention can be used as a screening device for initial, non-radiation involving, low-cost exam where, if the result is positive, a higher functionality version of the invention is used (for example, one with full display capabilities) and/or other techniques such as mammography, Magnetic Resonance Imaging, Positron Emission Tomography, and ultrasound. For screening purposes it is usually important to adjust the detection level so that the results are biased to having false positives and avoiding false negatives since the false positive tests can be followed up more intensively, or, in some cases, by repetition of the initial type of test. One can adjust relationships among true positives and negatives and false positives and negatives. Specificity and sensitivity can be adjusted as well.

An important approach to the testing of such devices is the ability of comparing the healthy tissue in one breast to a potential lesion in the other breast in the same patient.

Figure 15A:
FIGS. 15A and 15B illustrate the test configuration for melanoma.
Figure 15B:
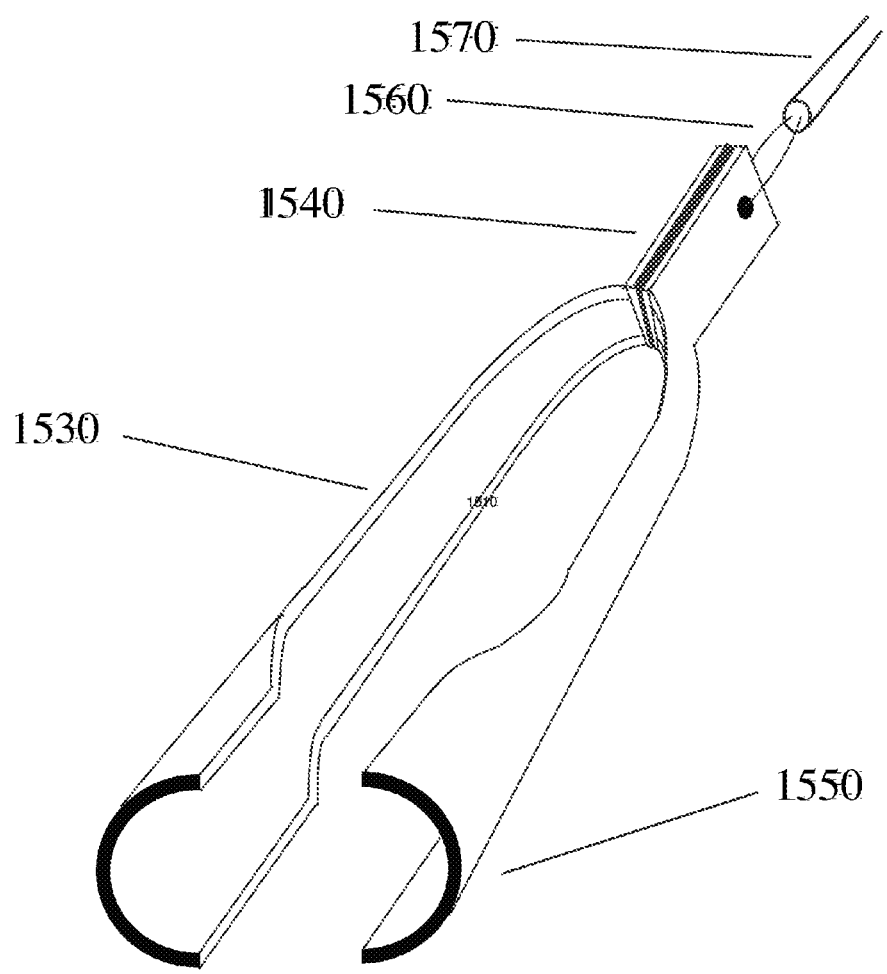

FIGS. 15 A and B show the test configurations for melanoma. FIG. 15A illustrates the test instrument applied to potential melanomas on the face with spring-action electrodes 1500 being applied with only the tips conductive and handle with wires 1510. FIG. 15B shows the electrode pair used to confine skin lesions as illustrated in FIG. 15A. Spring-action electrodes 1530 have exposed semicircular electrodes 1550 at the tips (one of which is the source electrode and the other the receiving electrode and which one is which is arbitrary). Spring-action electrodes 1530 are covered by insulation 1540 and are connected to the electronic instrumentation by wires 1560 and become embedded in cable 1570. In one embodiment, the semicircular electrodes are between 7 to 12 millimeters in diameter and separated up to 15 mm. The electrodes are insulated so they can touch each other if pushed together without shorting.

Figure 16:
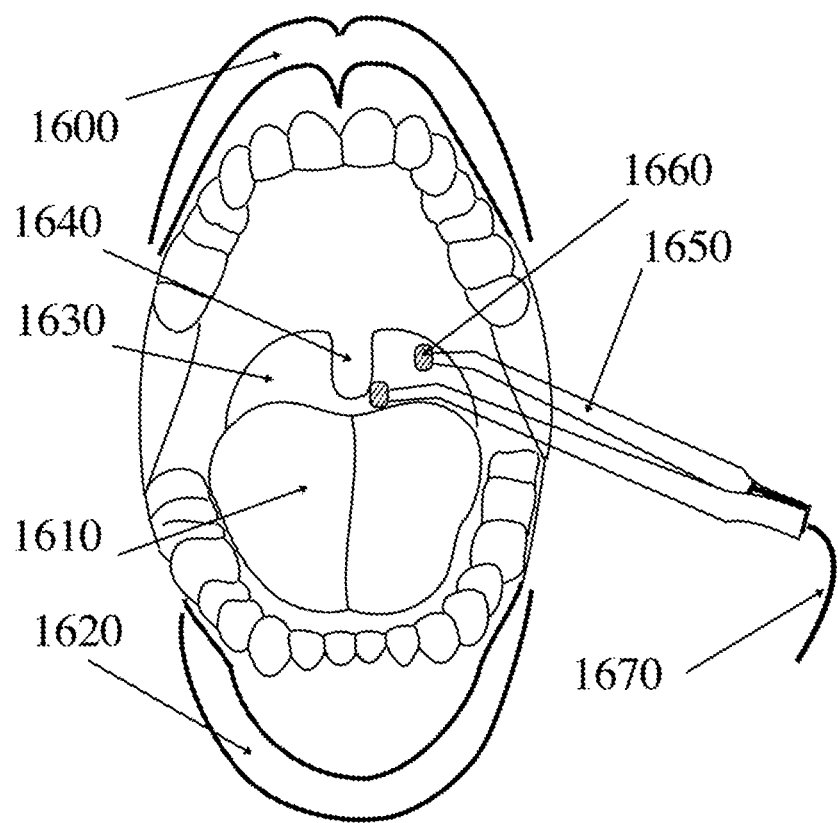
FIG. 16 illustrates the test configuration for the oral cavity.

FIG. 16 shows the oral cavity with such structures as the upper lip 1600, lower lip 1620, tongue 1610, tonsil 1630, and uvula 1640. The oral cavity is accessible and lesions often superficial. The impedance-measurement interface consists of a tweezers-style electrode pair 1650 insulated to the electrode active areas 1660 with source and receiving electrodes (which one is which does not matter) connected to cable 1670. The impedance-measurement interface can be applied any of the mentioned structures but any other included structures such as the mucosa of the cheeks, the gingiva, or the oral pharynx. If an area such as the tongue is sensitive, the area being measured can first have an anesthetic topically applied.

Figure 17A:
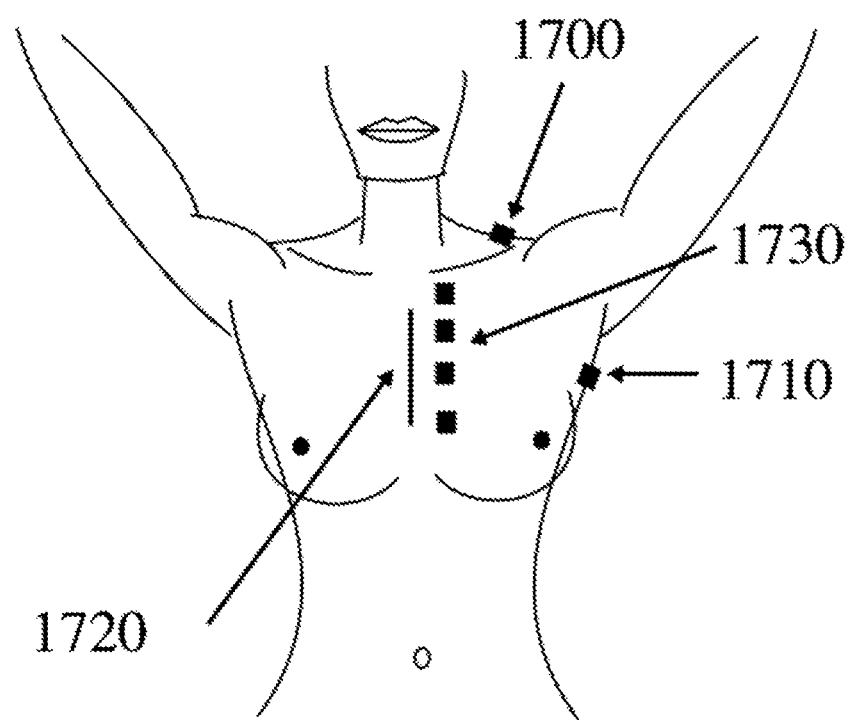
FIG. 17A and 17B illustrate the test configuration for the lung.
Figure 17B:
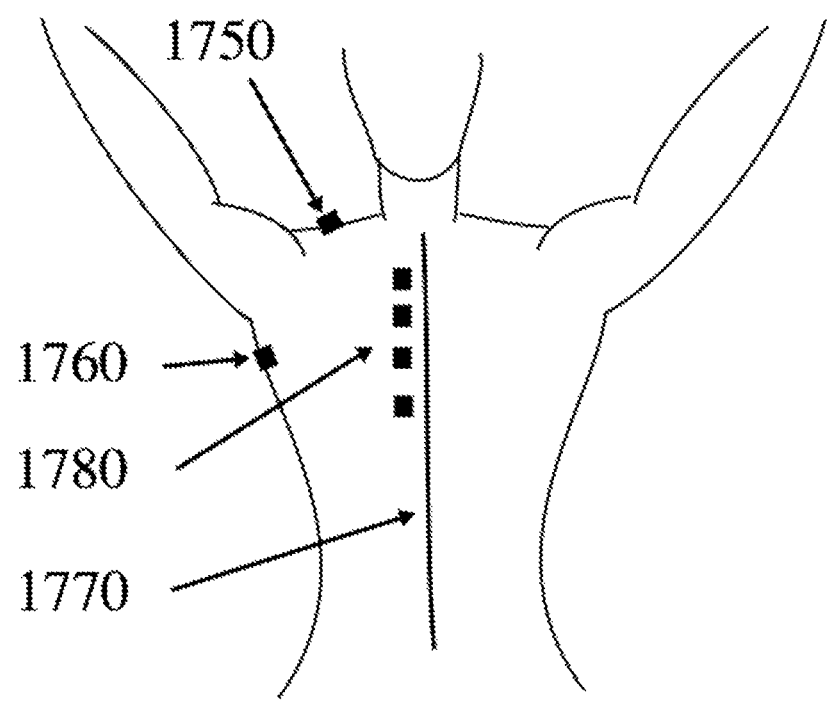
Figure 18:
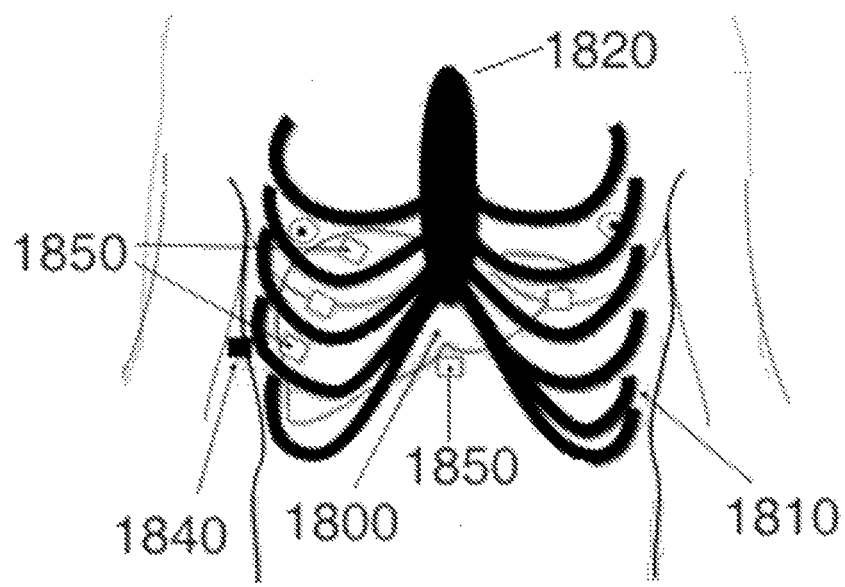
FIG. 18 illustrates the test configuration for the liver.

FIG. 17 shows the testing configuration for the lung. Measurements can be made on the anterior of the patient as shown in FIG. 17A or the posterior surface as shown in FIG. 17B. In FIG. 17A, source electrode 1700 can be preferentially located above the shoulder just posterior to clavicle or at position 1710 on the lateral surface of the side of the thorax being examined, in this case the left side of the patient. The receiving electrodes 1730 are located laterally to sternum 1720 located in the midline. Any if the electrodes are to be placed in the intercostal spaces or other areas (e.g., posterior to the clavicle) to minimize the interference of underlying cartilage or bone. FIG. 17B covers impedance measurements on the posterior surface of the patient. In FIG. 17B, source electrode 1750 can be preferentially located above the shoulder just posterior to clavicle or at position 1760 on the lateral surface of the side of the thorax being examined, in this case the left side of the patient. The receiving electrodes 1780 are located laterally to spine 1770 located in the midline FIG. 18 shows the test configuration for the liver. In FIG. 18, liver 1800 is contained within rib cage 1810 anchored by sternum 1820 with source electrode 1840 placed laterally on the side of the patient (or with alternative position at the position of the receiving electrode 1850), typically also posteriorly, with receiving electrodes (suggested to be) the source electrode 1850 (open-square symbols) placed over the surface of the skin overlying liver 1800. As was true for the lung above, the source and receiving electrodes are placed in the intercostal spaces or below the rib cage if the liver protrudes inferiorly to the rib cage to avoid interference by cartilage or bone.

Figure 19:
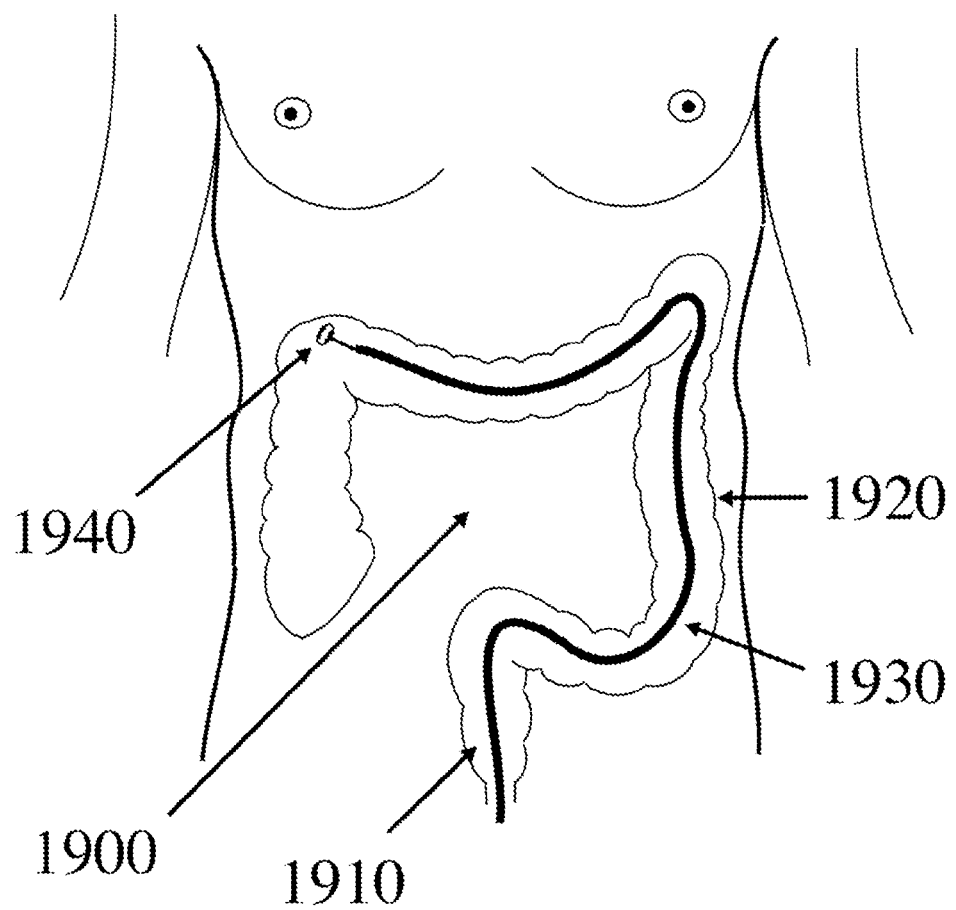
FIG. 19 illustrates the test configuration for the colon or rectum.

FIG. 19 shows the test configuration for the colon or rectum. Inside abdomen, 1900 is rectum 1910 and colon 1920. Specially outfitted colonoscope 1930 is threaded through the anus through rectum 1910 and the body of colon 1930 to the lesion of be assessed at location 1940 at which a semicircular electrode configuration of the type shown in FIG. 15B with one of the semicircular electrodes being the source electrode and the other the receiving electrode. The semicircular electrodes can be applied to lesions within the rectum as well as those within the colon.

Figure 20:
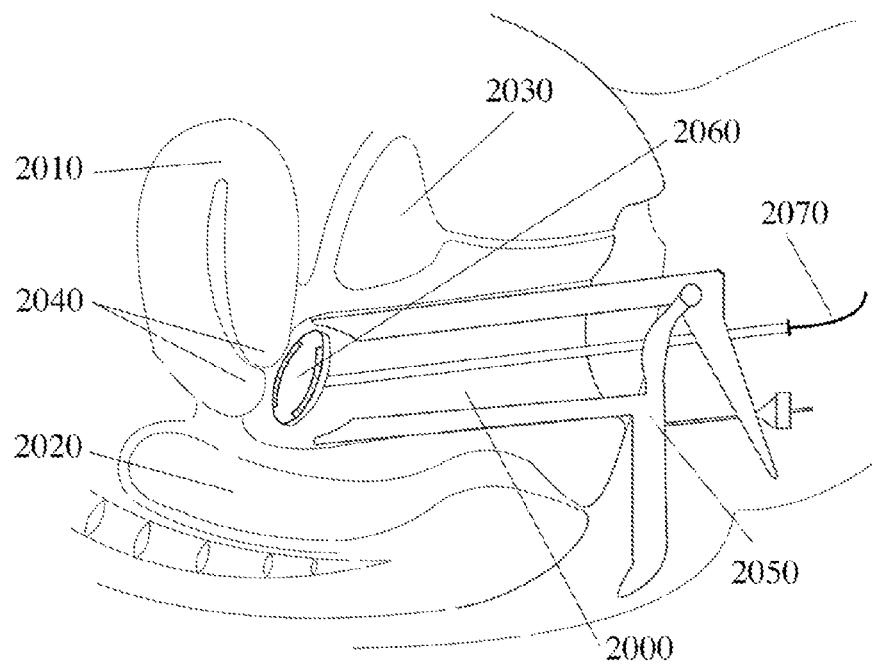
FIG. 20 illustrates the test configuration for the cervix.

FIG. 20 shows the test configuration for the cervix in the context of a cross section of the pelvis. The organs shown are the vagina 2000, the uterus 2010, rectum 2020, bladder 2030, and cervix 2040. To analyze cervix 2040, instrumented speculum 2050 is introduced through vagina 2000 and semicircular electrodes 2060 are applied to lesions on cervix 2040 with the electrodes connected to the impedance analyzer through wires 2070. The same instrumentation can be applied to masses in the vaginal cavity other than the cervix. The vaginal cavity is accessible and lesions often superficial.

Figure 21B:
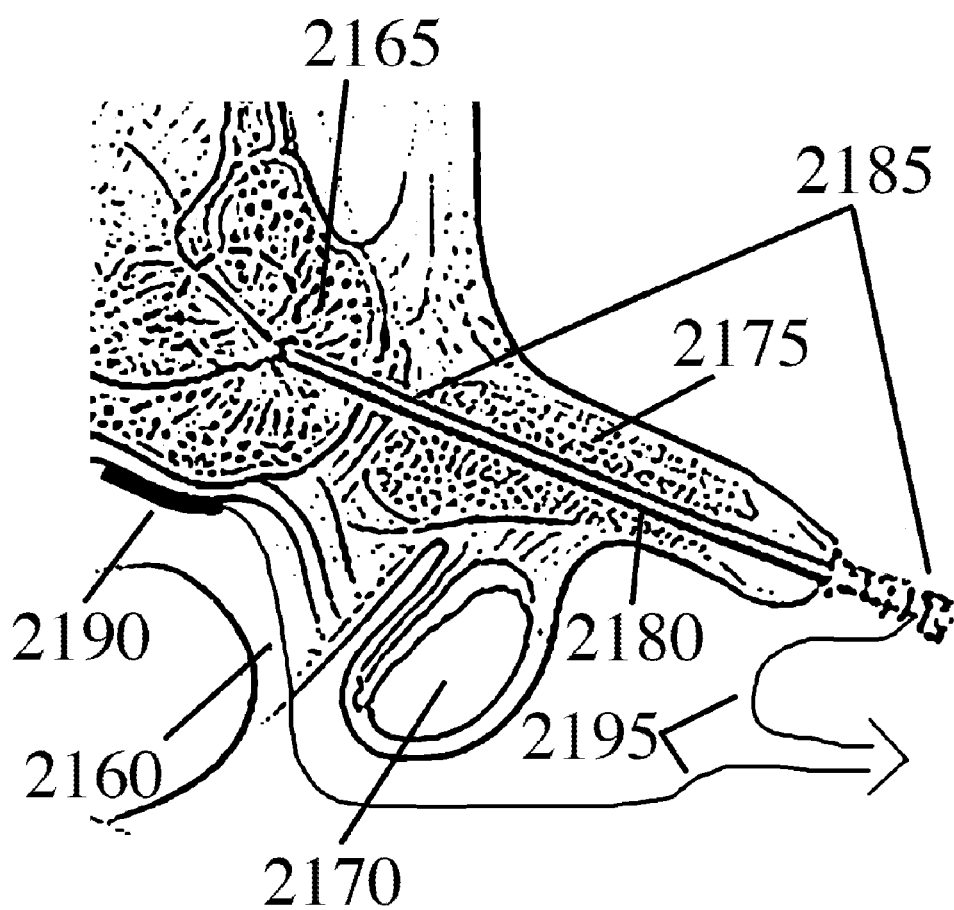
FIGS. 21A and 21B illustrate alternative test configurations for the prostate.
Figure 21A:
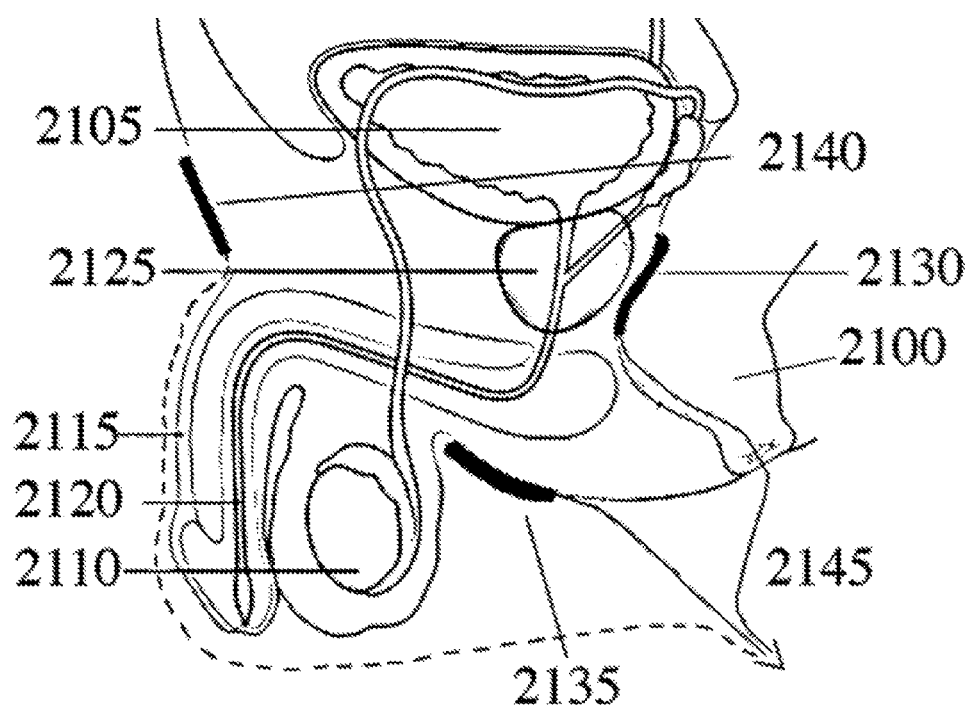

FIG. 21 shows test configurations for the prostate with FIG. 21A and FIG. 21B illustrating alternative electrode configurations. Organs shown in the vertical section of FIG. 21A are rectum 2100, bladder 2105, testis 2110, penis 2115, urethra 2120, and prostate gland 2125. The source electrode 2130 provides one side of the impedance analysis circuitry and receiving electrode 2135. Alternatively, the receiving electrode could be located at a different position 2140. Source electrode 2130 and one or both of receiving electrodes 2135 and 2140 are connected with the impedance analysis instrument (not shown) by wires 2145. FIG. 21B shows a vertical section through the male pelvic region demonstrating an alternative mechanism for doing the impedance measurement and analysis. The organs illustrated are the rectum 2160, prostate 2165, testis 2170, penis 2175, and urethra 2180. In this embodiment, the source electrode 2185 is placed in urethra 2180 and the receiving electrode 2190 are both connected to the impedance analysis instrument (not shown) by wires 2195.

Figure 22:
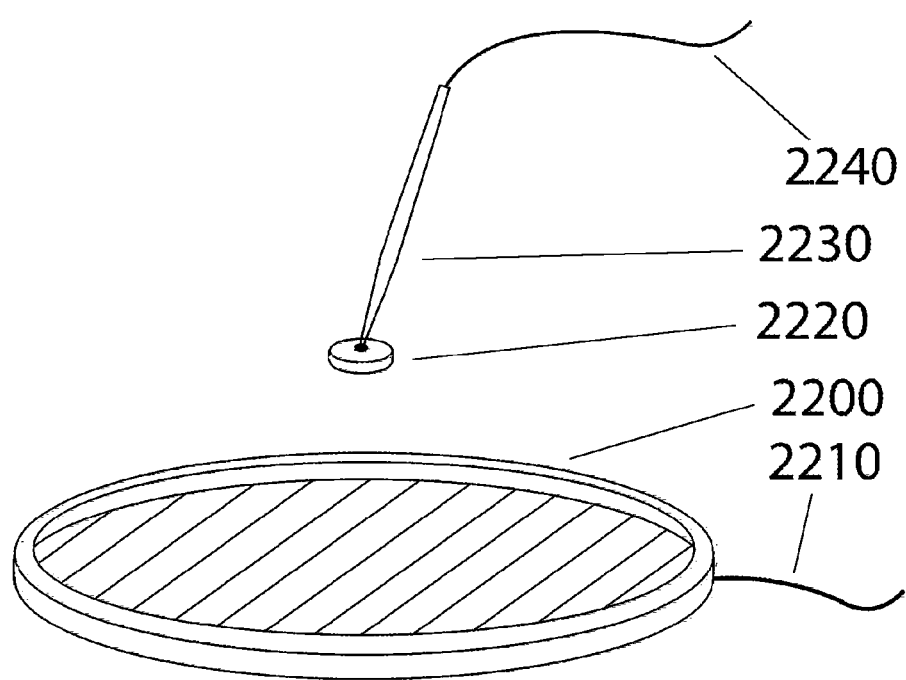
FIG. 22 illustrates the test configuration for tissue biopsy specimens.

FIG. 22 shows the test configuration for performing impedance analyses of biopsied tissue samples. The source electrode is a plate 2200 on which the tissue sample is placed and is connected to the impedance analysis instrument (not shown) by wire 2210. Plate 2200 is only conductive on the top surface; the sides and bottom are insulated. The tissue sample has its bottom resting on source electrode plate 1900 and the top of the sample has a receiving electrode 2220, typically a disk 7 to 15 mm in diameter pressed into it. Receiving electrode 2220 is secured to insulated handle 2230. Wire 2240 connects receiving electrode 2220 to the impedance analysis instrument (not shown). The surfaces of the plate 2200 or receiving electrode 2220 may be flat, curved, or an arbitrary shape.

While the approach described is applied to breast tissue, the same techniques with the same parameters can be applied for detecting abnormalities in other tissues, including, but not limited to, for example, lung and prostate tissue, using suitable source and receiving electrodes.

It is noted that any embodiment described herein for exemplary purposes is, of course, subject to variations. Because variations and different embodiments may be made within the scope of the inventive concept(s) herein taught, it is to be understood that the details herein are to be interpreted as illustrative and not in a limiting sense.

The invention claimed is:

1. A method for testing presence, characterization, and tracking of benign or malignant masses the method comprising:
    a. applying a wide range coherent frequency stimulation source signal with voltage receiving electrodes attached one of more first locations on or in the patient,
    b. measuring a wide-band current tissue response signal to the applied source signal with a current source electrode placed at one or more second locations on or in the patient;
    c. with a computer program stored on a non-transient computer medium executed by a processor, performing the steps of:
        a. correlating the measured tissue response signal with the applied source signal;
        b. calculating a transform selected from the group consisting of Fast Fourier Transform, Discrete Fourier Transform, Chirp-Z Transform, Wavelet Transform and Discrete Wavelet Transform of the correlated source signal and tissue response signal to determine a ratio-metric measurement;

c. comparing the determined ratio-metric measurement with derived ratios created in clinical studies indicative of healthy, benign and malignant tissue;

d. classifying the determined ratio-metric measurement as one of healthy, benign, and malignant tissue based on the comparison of the determined ratio with the derived ratios;

e. locating a mass, if present, based on the origin of the tissue response signal; and indicating the results to the user.

2. The method of claim 1 wherein the wide range frequency stimulation is used from with even and odd harmonics is selected from the group consisting of 20 kHz to 1 MHz, 1 MHz to 100 MHz, and 100 MHz to 10 GHz coherently sampled between the output stage and wide-band current measurement input.

3. The method of claim 1 wherein the excitation waveform of the applied stimulation source signal is selected from the group consisting of square wave, sine wave, and triangle wave.

4. The method in claim 1 wherein the indicating the results to the user comprises:

indication of the presence of an abnormality selected from the group consisting of auditory cue, vibratory cue, simple visual cue of either binary or relative magnitude, including level of probability, intermediate visual display presenting text or graphical results, including level of probability, and complex visual cue display presenting raw data and processed graphical information, including level of probability.

5. The method in claim 1 used in screening where if a result is positive, confirmation is sought by use of a technique selected from the group consisting of mammography, Magnetic Resonance Imaging, Positron Emission Tomography, ultrasound, and tissue histology.

6. The method in claim 1 where adjustments are made in parameters selected from the group consisting of specificity, sensitivity, true positives, false positives, true negatives, and false negatives.

7. The method in claim 1 applied to breast masses in which a. one or a plurality of source electrodes attached where a breast joins the chest wall of a patient, b. a receiving electrode attached to the nipple of the same patient.

8. The method in claim 1 applied to prostate masses in which c. one or a plurality of receiving electrodes are attached to the perineal skin in close proximity to the underlying prostate of the patient, and d. a source electrode is placed in the urethra at the level of the patient's prostate.

9. The method in claim 1 applied to masses in directly accessible superficial organs selected from the group consisting of skin, oral cavity, vaginal cavity, rectum, and colon in which a. the receiving electrode is a semicircle that is one half of a circular electrode pair applied to surround a patient lesion, and b. a source electrode is a semicircle that is the other half of the circular applied to surround the patient lesion.

10. The method in claim 1 applied to lung masses in which a. one or a plurality of receiving electrodes are attached to the parasternal skin in the intercostal spaces on the side of the thorax being analyzed with complementary positions on the back of the patient, and b. the source electrode at the one or more positions on the side to be analyzed selected from the group consisting of lateral thorax and the top of the thorax posterior to the clavicle.

11. The method in claim 1 applied to liver masses in which a. one or a plurality of receiving electrodes attached to the skin over the liver in the intercostal spaces, and b. a source electrode at a position selected from the group consisting of in an intercostal space on the lateral right and just under the lower part of the sternum.

12. The method in claim 1 for testing of benign or malignant tissue biopsy specimens, the method comprising:

a. one or a plurality of receiving electrodes on one face of a tissue biopsy specimen, and b. a source electrode located on the opposite face of the tissue biopsy specimen.

* * * * *